United States Patent
Wheatley et al.

(12)

(10) Patent No.: US 6,197,307 B1
(45) Date of Patent: Mar. 6, 2001

(54) METHOD FOR PRODUCING HIGH ACTIVITY EXTRACTS FROM *HARPAGOPHYTUM PROCUMBENS*

(75) Inventors: Gary William Wheatley, Hull; Thomas Brian Chapman, Brough; Suzanne Dring, Brough; Nigel Gericke, Brough, all of (GB)

(73) Assignee: Essential Nutrition, Ltd., Brough (GB)

( * ) Notice: Subject to any disclaimer, the term of this patent is extended or adjusted under 35 U.S.C. 154(b) by 0 days.

(21) Appl. No.: 09/280,499

(22) Filed: Mar. 30, 1999

(51) Int. Cl.7 .................................................. A61K 35/78
(52) U.S. Cl. ............................................................ 424/195.1
(58) Field of Search ........................................... 424/195.1

(56) References Cited

U.S. PATENT DOCUMENTS

| 4,554,170 | * | 11/1985 | Panzner et al. . |
| 4,968,787 | * | 11/1990 | Inada et al. . |
| 4,985,265 | * | 1/1991 | Duboc et al. . |
| 5,733,551 | * | 3/1998 | Jacob et al. . |
| 5,929,038 | * | 7/1999 | Chang . |

FOREIGN PATENT DOCUMENTS

| 62-000496 | | 6/1987 | (JP) . |
| 9205686 | * | 7/1992 | (KR) . |
| 9734565 | * | 10/1997 | (WO) . |
| 9744051 | * | 11/1997 | (WO) . |

OTHER PUBLICATIONS

PDR for Herbal Medicines, pp. 888–889, Jan. 1998.*
Grimmett, C. Chemistry and Industry—food processing. vol. 10, pp. 359–362, 1993.*
Hawley, G. The Condensed Chemical Dictionary, Van Nstrand Reinhold Co., p. 1000, 1981.*
Ouellette, R. Intro. Gen. Org. Biol. Chem., 2nd ed., Macmillan Publ. Co., p. 545, 1993.*
Moyler, Extr. of Essential Oils w/Carbon Dioxide, *Flavor & Frag. J.*, 8, pp. 235–247, 1993.
CAS Online Abstract No. 127:166771, and DE 19603788 A1 (Chrubasik), see p. 1, lines 46–47.
CAS Online Abstract No. 111:180743, and FR 2614791 A1 (Moati), see especially p. 3, Paras 5 & 6.
CAS Online Abstract No. 127:268011, and WO 97/34565 A1 (Stumpf et al.), see Beispeil 2, 3, 5 & 7; p. 2, para 4; see also WPI Abstract Accession No. 97–479962 [44].
Plant. Med. Phytother. vol. 12, No. 3, 1978; M Haag–Berrurier, pp. 197–206, see especially "Resultats", pp. 203–204; see also CAS Online Abstract No. 90: 76624.

* cited by examiner

*Primary Examiner*—Christopher Tate
(74) *Attorney, Agent, or Firm*—Jenkens & Gilchrist

(57) ABSTRACT

A novel extract from the root of *Harpagophytum procumbens* (Devil's Claw) which contains high levels of the compound harpagoside and a method for producing the extract.

11 Claims, No Drawings

METHOD FOR PRODUCING HIGH ACTIVITY EXTRACTS FROM *HARPAGOPHYTUM PROCUMBENS*

This invention relates to a novel extract from the root of *Harpagophytum procumbens* (Devil's Claw) that contains high levels of the compound harpagoside. Harpagoside exhibits anti-inflammatory and analgesic activity in standard animal modes. The invention also relates to a method of producing such an extract.

Preparations derived from the root of *Harpagophytum procumbens* (also known as Devils Claw) have traditionally been used in the symptomatic treatment of chronic inflammatory diseases such as rheumatism and arthritis. The widespread use of preparations of devils claw and their generally accepted efficacy and safety has been recognised by the introduction of an official monograph into both the 3$^{rd}$ Edition of the European Pharmacopoeia and the current British Pharmacopocia. Extracts derived from Harpagophytum have been demonstrated to exhibit significant anti-inflammatory activity and analgesic activity in a range of standard in vivo animal models (M C Lanhers et al, *Planta Medica*, 58 117–123 (1992)). The above pharmacological activity was much more pronounced in chronic models rather than short term acute studies (R Grahame & B V Robinson, *Ann Rheum Dis*, 40, 632 (1981)).

In several of the studies, samples of pure harpagoside (an iridoid glycoside isolated from Harpagophytum root) (F C Czygan & A Kruger, *Planta Med*, 31 305–307 (1997)) also exhibited comparable pharmacological activity to that observed for the crude Harpagophytum extracts indicating that this is probably the active constituent (O Eichler & C Koch *Arnzheim Forsch*, 20, 107–109 (1970)). These experimental indications of efficacy have been largely confirmed by several clinical trials which revealed statistically significant improvements in the symptoms of rheumatic disease for Harpagophytum extracts usually standardised on harpagoside content (S C Chrubasik, *Phytomedicine* 3 (1), 1–10 (1997) and P Belaiche, *Phytotherapy*, 1, 22–28 (1982)).

The central importance of harpagoside in ensuring the efficacy of Harpagophytum preparations is emphasized by the European Pharmacopoeia monograph stipulating a minimum harpagoside content of 1.2% W/W for Harpagophytum root which is to be used medicinally (*European Pharmacopoeia*, 3$^{rd}$ Edition, P716–717 (1997)).

In addition, to the harpagoside and other related iridoid glycosides, the root of *Harpagophytum* contains large quantities of simple sugars such as stachyose and sucrose ("*British Herbal Compendium*", Vol 1, Ed P R Bradley, BHMA (1992) (p78–82)). This has the result of producing very large extractive values of up to 70% (70 g of extract from 100 g raw herb) when aqueous or aqueous-alcoholic extraction is employed.

This is reflected in the specification of the best commercially available extracts which have an extractive value of around 40% and harpagoside content of only approximately 2.1% W/W approximately.

The large mass of extract produced per gramme of herb is unsatisfactory as this has the effect of diluting the concentration of the extracted harpagoside, resulting in unrealistically high dose of extract being required to administer an effective dose of harpagoside. The large number of tablets that this corresponds to has unfavourable implications for patient compliance and hence efficacy.

A further problem associated with the medicinal use of Harpagophytum extracts is the sensitivity of the active components to degradation by stomach acid. Thus, a study comparing the effect of the route of administration of Harpagophytum extract on the anti-inflammatory action in test animals demonstrated the same extract to be very active by intraperitoneal injection by completely ineffective when given orally (M C Lanhers et al, *Planta Medica*, 58 117–123 (1992)).

An in vitro study produced similar results showing loss of previously demonstrated anti-inflammatory activity after an extract had been treated with 0.1M hydrochloric acid (R Soulimani et al, *Can J Physiol Pharmacol*, 72, 1532–1536 (1992)).

In recent years, extraction using liquefied carbon dioxide has been applied to production of fractions rich in biologically active compounds from plant based raw materials (European Patent EP58365; European Patent EP553658; and D A Moyler, *Flav & Frag J*, 8 235–247 (1993)).

Liquid carbon dioxide has a high selectivity, being able to solubilise low molar mass compounds of moderate polarity whilst leaving behind in the matrix higher molecular weight lipids, waxes and pigments which would otherwise increase the bulk of an extract and dilute the actives content (G Wilke *Angew, Chem Int Eng Ed* 17, 710 (1978)). Liquid carbon dioxide is also superior to non-polar organic solvents in that it is non-flammable, so that the solvent can be safely vented to the atmosphere avoiding waste disposal and recycling costs. The intrinsically non-toxic and highly volatile nature of carbon dioxide avoids any problems of elimination of residual levels of harmful solvents from the product.

According to a first aspect the present invention provides a method of preparation of an extract containing harpagoside comprising the step of extracting Harpagophytum root with liquid carbon dioxide and allowing the carbon dioxide to evaporate from the resultant mixture.

According to a second aspect of the invention there is provided an extract from Harpagophytum root containing an amount of more than 3%, preferably more than 5%, particularly preferably more than 7%, especially preferably more than 9% by weight of harpagoside, the extract not containing any residual solvent.

The resultant residual extract contains a higher percentage of harpagoside than may be obtained by solvent extraction using aqueous alcoholic mixtures.

A co-solvent may be employed in the method of the invention for example a polar hydroxylic solvent such as a $C_{1-4}$-alcohol, preferably ethanol. The co-solvent is preferably present in an amount in the range 1–20%, preferably 5–15%, particularly preferably about 10% by weight. Preferred methods of the invention employ a co-solvent as this has been found to give proportions of harpagoside typically greater than 9%.

Preferred methods of extraction are carried out at a pressure in the range 1400–5000 psi (96 to 343 bar), particularly preferably at about 4000 psi (276 bar).

Use of a pressure of 1400 to 4000 psi, preferably 1400 to 1500 psi at a temperature of 20–45° C. is preferred.

According to a further aspect of the invention there is provided a pharmaceutical composition comprising an extract according to the invention together with one or more physiologically acceptable carriers or excipients. Preferably, the composition is orally administrable and for this purpose is preferably provided with an enteric coating (e.g. cellulose acetate phthalate).

The invention is further described by means of example by not in any limitative sense.

EXAMPLE

Roughly ground root of Harpagophytum procumbens was packed into a suitable pressured vessel. A volume of liquid carbon dioxide at the ratio approximately 10 ml of liquid carbon dioxide per 1 g of herb was allowed to pass through the raw material at a flow rate of approximately 2 ml/min. The liquid carbon dioxide was than collected, the pressure released and carbon dioxide allowed to vent to the atmosphere. Removal of any added co-solvent or residual moisture was completed by drying in a vacuum desiccator. The residual extract in the collection vessel was an oil or semi-solid depending on the exact extraction conditions.

The following range of extraction conditions were employed:

| SAMPLE | PRESSURE | TEMP | CO-SOLVENT | % YIELD | % W/W HARPAGOSIDE |
|---|---|---|---|---|---|
| DC1 | 1500 | 27° C. | NONE | 0.4% | 0% |
| DC2 | 1500 | 27° C. | 1% | 0.8% | 0.03% |
| DC3 | 4000 | 41° C. | NONE | 0.4% | 0% |
| DC4 | 4000 | 41° C. | 1% | 0.4% | 1.6% |
| DC5 | 4000 | 41° C. | 10% | 1.5% | 10.0% |

The harpagoside content was determined by an HPLC method based on that described in the monograph for Devils Claw (Harpagophytum) in the Third Edition of the European Pharmacopoeia.

The harpagoside content of the Harpagophytum root starting material was determined to 0.9% by the same European Pharmacopoeia method.

Sub-critical liquid $CO_2$ (25° C./1500 psi) liquid $CO_2$ close to the critical temp (36° C./1440 psi) and supercritical $CO_2$ significantly above the critical temperature (36° C./4000 psi) gave products containing limited proportions of harpagoside.

The addition of 10% ethanol co-solvent has been found to significantly increase the content of harpagoside compared to the use of pure liquid carbon dioxide.

The use of supercritical carbon dioxide combined with 10% ethanol co-solvent yields the maximum concentration of harpagoside in the extract and thus represents the preferred embodiment of the invention.

For the purposes of producing tables the extract is dissolved in the minimum quantity of ethanol and absorbed on to an inert pharmaceutical excipient, preferably Maltodextrin, and the solvent allowed to evaporate at room temperature. In the preferred embodiment of the invention 15 g of extract is absorbed per 100 g of Maltodextrin.

The extract adsorbate may then be mixed with pharmaceutical excipients and compressed into tablets using a rotary tablet press.

The following direct compression formulation represents a suitable example of a tablet mixture:

| 100 mg | Harpagophytum extract adsorbate |
| 194 mg | Direct Compression Lactose |
| 50 mg | Microcrystalline Cellulose |
| 50 mg | Pre-gelatinised Starch |
| 2 mg | Magnesium Stearate |
| 2 mg | Stearic acid |
| 2 mg | Amorphous Silica |
| 400 mg | |

The tablets are then coated with a suitable enteric coating solution. In the preferred embodiment of the invention a solution of cellulose acetate phthalate is employed, to protect them from degradation by stomach acid. Typically, 10% by weight of cellulose acetate phthalate is applied to the tablet cores as a solution in acetone/isopropanol in a heated rotary coating pan.

This produces a table containing Harpagophytum extract equivalent to 1 g of whole herb.

What is claimed is:

1. A method for preparing an extract containing harpagoside comprising the steps of extracting Harpagophytum root with subcritical or supercritical carbon dioxide and a co-solvent and allowing the carbon dioxide to evaporate from the resultant mixture, wherein the resultant mixture comprises at least 5 wt % of harpagoside.

2. A method as in claim 1, wherein the carbon dioxide is super-critical carbon dioxide.

3. A method as in claim 1 in which the co-solvent is a polar hydroxylic solvent.

4. A method as in claim 3, wherein the carbon dioxide is super-critical carbon dioxide.

5. A method as in claim 1, in which the co-solvent is a $C_{1-4}$ alcohol.

6. A method as in claim 5, wherein the carbon dioxide is super-critical carbon dioxide.

7. A method as in claim 5, in which the alcohol is ethanol.

8. A method as in claim 7, wherein the carbon dioxide is super-critical carbon dioxide.

9. The method of claim 1, wherein the resultant mixture comprises at least 7 wt % of harpagoside.

10. The method of claim 1, wherein the resultant mixture comprises at least 9 wt % of harpagoside.

11. The method of claim 1, wherein the resultant mixture comprises about 10 wt % of harpagoside.

* * * * *